United States Patent
Wang et al.

(10) Patent No.: US 12,290,615 B2
(45) Date of Patent: May 6, 2025

(54) DRUG COATED BALLOON AND PREPARATION METHOD THEREOF

(71) Applicant: BROSMED MEDICAL CO., LTD., Guangdong (CN)

(72) Inventors: Liwei Wang, Guangdong (CN); Junyi Huang, Guangdong (CN); Zhijun Zhang, Guangdong (CN); Bin Li, Guangdong (CN)

(73) Assignee: BROSMED MEDICAL CO., LTD., Dongguan (CN)

( * ) Notice: Subject to any disclaimer, the term of this patent is extended or adjusted under 35 U.S.C. 154(b) by 0 days.

(21) Appl. No.: 18/414,450

(22) Filed: Jan. 16, 2024

(65) Prior Publication Data
US 2024/0148943 A1    May 9, 2024

Related U.S. Application Data

(63) Continuation-in-part of application No. PCT/CN2023/082108, filed on Mar. 17, 2023.

(30) Foreign Application Priority Data

Sep. 22, 2022  (CN) .......................... 202211169429.4

(51) Int. Cl.
| | | |
|---|---|---|
| A61L 29/16 | (2006.01) | |
| A61L 29/04 | (2006.01) | |
| A61L 29/08 | (2006.01) | |

(52) U.S. Cl.
CPC ............. A61L 29/16 (2013.01); A61L 29/049 (2013.01); A61L 29/085 (2013.01);
(Continued)

(58) Field of Classification Search
CPC .. A61L 29/16; A61L 29/085; A61L 2300/416; A61L 2300/602; A61L 2300/608
See application file for complete search history.

(56) References Cited

U.S. PATENT DOCUMENTS

| | | | |
|---|---|---|---|
| 8,778,379 B2 * | 7/2014 | Doshi | ................ A61L 27/54 |
| | | | 424/423 |
| 9,034,363 B2 * | 5/2015 | Doshi | .................. A61P 7/02 |
| | | | 424/424 |

(Continued)

FOREIGN PATENT DOCUMENTS

| | | |
|---|---|---|
| CN | 1883720 A | 12/2006 |
| CN | 102869393 A | 1/2013 |

(Continued)

OTHER PUBLICATIONS

Miao Li-Fu et al., Rapamycin-loaded Poly (lactic-co-glycolic) Acid Nanoparticles for Intraarterial Local Drug Delivery: Preparation, Characterization, and in vitro/in vivo Release, Journal of ACTA Academiae Medicinae Sinicae, Aug. 31, 2008, pp. 491-497, vol. 30, No. 4.

(Continued)

*Primary Examiner* — Nathan R Price
*Assistant Examiner* — Adam J. Cermak

(57) ABSTRACT

A drug coated balloon includes a balloon body and a drug loaded coating layer. The drug loaded coating layer includes a first drug loaded coating component having at least two controllable sustained release drugs with different drug release kinetics, and a second drug loaded coating component including an active drug. The second drug loaded coating component is dispersed among the controllable sustained release drugs and couples the controllable sustained release drugs on the balloon body. The first and second drug loaded coating components are both non-hydrophilic compositions. The drug coated balloon provides sufficient initial drug loading dosage to the lesion site, and has adjustable drug release rate, thereby allowing the drug coated balloon to provide bioactive drugs to the treatment site at different stages of the cascade reaction of vascular (Continued)

restenosis, providing the controllable long-acting therapeutic drugs, and improving the overall vascular drug release efficacy.

10 Claims, 2 Drawing Sheets

(52) U.S. Cl.
CPC ... *A61L 2300/216* (2013.01); *A61L 2300/416* (2013.01); *A61L 2300/602* (2013.01); *A61L 2300/608* (2013.01); *A61L 2300/62* (2013.01); *A61L 2420/02* (2013.01); *A61L 2420/06* (2013.01)

(56) References Cited

U.S. PATENT DOCUMENTS

| | | | |
|---|---|---|---|
| 9,415,142 B2* | 8/2016 | DeYoung | A61L 31/10 |
| 9,492,594 B2* | 11/2016 | Ahlering | A61P 9/14 |
| 9,510,856 B2* | 12/2016 | McClain | A61L 29/085 |
| 9,782,516 B2* | 10/2017 | Pacetti | A61L 27/3604 |
| 9,949,957 B2* | 4/2018 | Slager | A61K 9/5138 |
| 10,117,972 B2* | 11/2018 | McClain | A61L 31/08 |
| 10,188,772 B2* | 1/2019 | McClain | A61L 29/085 |
| 10,213,528 B2* | 2/2019 | Slager | A61L 29/14 |
| 10,213,529 B2* | 2/2019 | Slager | A61L 29/16 |
| 11,202,754 B2* | 12/2021 | Naga | A61P 25/04 |
| 11,406,742 B2* | 8/2022 | Ahlering | A61K 31/436 |
| 2004/0086542 A1* | 5/2004 | Hossainy | A61L 29/085 427/2.28 |
| 2005/0060020 A1* | 3/2005 | Jenson | A61F 2/07 623/1.42 |
| 2005/0192657 A1* | 9/2005 | Colen | A61F 2/82 623/1.42 |
| 2006/0045901 A1* | 3/2006 | Weber | A61L 31/16 424/426 |
| 2008/0195079 A1 | 8/2008 | Moore et al. | |
| 2008/0255509 A1* | 10/2008 | Wang | A61L 31/08 623/1.46 |
| 2010/0070013 A1* | 3/2010 | Park | A61F 2/86 623/1.42 |
| 2010/0076377 A1* | 3/2010 | Ehrenreich | A61L 29/085 604/93.01 |
| 2011/0144582 A1* | 6/2011 | Stankus | A61L 29/085 604/103.02 |
| 2012/0083734 A1* | 4/2012 | Ayres | A61L 29/14 604/500 |
| 2012/0277726 A1* | 11/2012 | Doshi | A61P 7/02 604/509 |
| 2014/0004170 A1* | 1/2014 | Krohen | A61L 31/10 427/2.24 |
| 2014/0046254 A1* | 2/2014 | Stankus | A61L 29/085 604/103.02 |
| 2015/0250926 A1* | 9/2015 | McClain | A61L 29/148 604/509 |
| 2016/0250452 A1 | 9/2016 | Wang | |
| 2018/0236139 A1* | 8/2018 | Raina | A61M 25/104 |
| 2019/0046693 A1* | 2/2019 | Ahlering | A61L 29/16 |
| 2022/0193310 A1* | 6/2022 | Labhasetwar | A61L 31/129 |
| 2023/0270680 A1* | 8/2023 | Fritz | A61K 33/24 424/489 |
| 2023/0293780 A1* | 9/2023 | Betts | A61L 31/16 424/423 |

FOREIGN PATENT DOCUMENTS

| | | | | |
|---|---|---|---|---|
| CN | 204182007 U | | 3/2015 | |
| CN | 104511084 A | | 4/2015 | |
| CN | 104841060 A | | 8/2015 | |
| CN | 108465129 A | | 8/2018 | |
| CN | 109985280 A | * | 7/2019 | ........... A61L 29/085 |
| CN | 110292701 A | * | 10/2019 | ............ A61L 29/08 |
| CN | 110882473 A | | 3/2020 | |
| CN | 113813449 A | * | 12/2021 | ........... A61L 29/085 |
| CN | 113893384 A | * | 1/2022 | ........... A61L 29/085 |
| CN | 114870096 A | | 8/2022 | |
| WO | WO-2020081455 A1 | * | 4/2020 | ........... A61K 31/436 |
| WO | WO-2022217398 A1 | * | 10/2022 | ........... A61L 29/085 |

OTHER PUBLICATIONS

Konstantinos Katsanos et al., Risk of Death Following Application of Paclitaxel-Coated Balloons and Stents in the Femoropopliteal Artery of the Leg: A Systematic Review and Meta-Analysis of Randomized Controlled Trials, Journal of the American Heart Association, Dec. 6, 2018.

* cited by examiner

DRUG COATED BALLOON AND PREPARATION METHOD THEREOF

CROSS REFERENCE TO RELATED APPLICATIONS

This application is a continuation-in-part application of International (PCT) Patent Application No. PCT/CN2023/082108 filed on Mar. 17, 2023, which claims priority from Chinese Patent Application No. 202211169429.4 filed on Sep. 22, 2022. The contents of the above-identified applications are incorporated herein by reference.

FIELD OF THE INVENTION

The present invention relates to the technology field of medical device, particularly to a drug coated balloon and a preparation method thereof.

BACKGROUND OF THE INVENTION

Percutaneous transluminal angioplasty has become a common choice for treating coronary and peripheral artery diseases. The balloon catheter enters the lesion site through the artery, and the balloon during the inflation process applies mechanical force to the lesion vessel to compress the plaque tissue against the arterial wall, to expand the vascular lumen and help to restore blood flow. Afterwards, the balloon is withdrawn from the blood vessel. In the case of drug coated balloons, the device not only mechanically dilates the narrowed vessel but also rapidly releases therapeutic drugs to the vessel wall, achieving localized drug delivery. Compared with drug-eluting stents placement, the drug coated balloon, as a novel treatment method under the concept of intervention rather than implantation, avoids the stacking placement of stents when applied to restenosis lesions within the stents and reduces the metal cage effect of permanent stent implantation on blood vessels. The use of the drug coated balloon also allows shorter duration of dual antiplatelet therapy and reduces thrombotic risk due to the absence of a permanent implant. At the same time, it has the advantages of strong operability, making it more conducive in dealing with other conditions like small vessel lesions.

There are also differences in the way drugs are delivered to the diseased blood vessel between the drug coated balloon and the drug eluting stent. Active drugs in the drug eluting stent are usually carried by polymers, and the composition of the polymer and the active drug coating determines the drug release mechanism and kinetics after stent implantation. The stent is implanted and retained in the target lesion site, and the drug is less likely to migrate to other locations in the body. In particular, for the single-sided abluminal coating stent, the drug coating is confined to the closely adjacent vascular wall and the outer surface of the stent. This allows for a slow, controlled release of the active drug to dissolve over time. The drug coated balloons only come into contact with the blood vessel wall for a short period of time. Within the few minutes or even seconds of balloon inflation, the necessary dose of the active drug needs to be released and transfer to the diseased vessel. After the balloon is withdrawn from the blood vessel, the active drug does not have a mode of in-situ retention similar to what is provided by a drug eluting stent. In addition, it's difficult for the drug coated balloons to have a stable polymer coating system due to its above application method, thus the loss of active drugs during tracking through the artery is not negligible. Based on the above factors, the drug coated balloons that have been approved and those mentioned in research literature generally have significantly higher drug doses compared to their corresponding drug-eluting stents. For example, the dose of the active drug, paclitaxel, in the SSED P180011 drug-eluting stent is even lower than one-tenth of the drug coated balloon SSED P190019.

The majority of drug coated balloons approved for clinical use are based on paclitaxel as the active drug, and a large number of clinical studies have provided evidence to support the safety and feasibility of using drug coated balloon (DCB). However, Dr. Katsanos et al. conducted a systematic analysis and statistics based on a large amount of clinical data, and their result was published in the Journal of the American Heart Association. They found that using paclitaxel as an active drug in the femoral and popliteal arteries of the lower limbs resulted in an increased risk of death. It took 5 years to review of the totality of the available data and analyses, and determined that the data does not support an excess mortality risk for paclitaxel-coated devices, even though there is still concern on the loss of paclitaxel crystal particles in the human body may pose a safety hazard especially for higher dose drug coated balloon.

As the standard drug for coronary artery disease treatment, sirolimus is widely recognized for its safety and effectiveness in the field of coronary drug delivery stents, as the active component of drug delivery balloons. However, due to the differences in its molecular structure and physicochemical properties compared to paclitaxel, sirolimus has lower lipophilicity, making it more challenging to transfer to the vascular vessel wall. This issue also makes the development of sirolimus coated balloon more challenging.

SUMMARY OF THE INVENTION

To overcome the shortcomings of existing technology, the objective of present invention is to provide a drug coated balloon and a preparation method thereof. The balloon is able to provide sufficient initial loading drug dosage to the lesion site, provide controllable long-acting therapeutic drugs to the lesion site, and improve the overall vascular drug release efficacy.

In order to achieve the above objectives, the present invention discloses a drug coated balloon, which includes a balloon body and a drug loaded coating layer coated on an outer surface of the balloon body. The drug loaded coating layer includes: a first drug loaded coating component including at least two controllable sustained release drugs with different drug release kinetics; and a second drug loaded coating component including an active drug in a free unbound form, which is dispersed among the controllable sustained release drugs the first drug loaded coating component and couples the controllable sustained release drugs component onto the balloon body. Both the first drug loaded coating component and the second drug loaded coatings component are non-hydrophilic compositions.

Compared with the existing technology, the drug coated balloon of the present invention includes a drug loaded coating in a non-hydrophilic structure coated on the outer surface of the balloon body, thereby ensuring the lipophilicity of the drug loaded coating, and ensuring the drug transfer ability to the vascular wall and the drug retention ability in the vascular inner wall upon blood wash-off. At the same time, the first drug loaded coating component includes at least two controllable sustained release drugs, and each of which has different drug release kinetics, thereby avoiding explosive drug release and extinction. Furthermore, the drug release rate can be adjusted through different combinations, so that the drug coated balloon can provide biologically active drugs to the treatment area at different stages of cascade reaction of vascular restenosis, thereby realizing the provision of controllable long-acting therapeutic drugs to the lesion site, and improving the overall vascular drug release efficacy. The drug coating also includes an active drug in a free unbound form, which can provide adequate initial loading drug dosage needed for blood vessel that may be damaged during angioplasty dilation.

Correspondingly, the present invention also provides a preparation method of a drug coated balloon, including the steps:

providing a balloon body;
preparing at least two controllable sustained release drugs and controlling each of the controllable sustained release drugs to have different drug release kinetics;
preparing an active drug in a free unbound form;
preparing a suspension spray coating solution by combining a proper ratio of the controllable sustained release drugs with the active drug in a coating solvent or a solvent combination; and
applying the suspension spray coating solution onto a surface of the balloon body.

DETAILED DESCRIPTION OF ILLUSTRATED EMBODIMENTS

To provide a detailed explanation of the technical content, structural features, achieved objectives, and effects of the present invention, the following is a detailed explanation combined with the implementation method and accompanying drawings.

Figure 1:
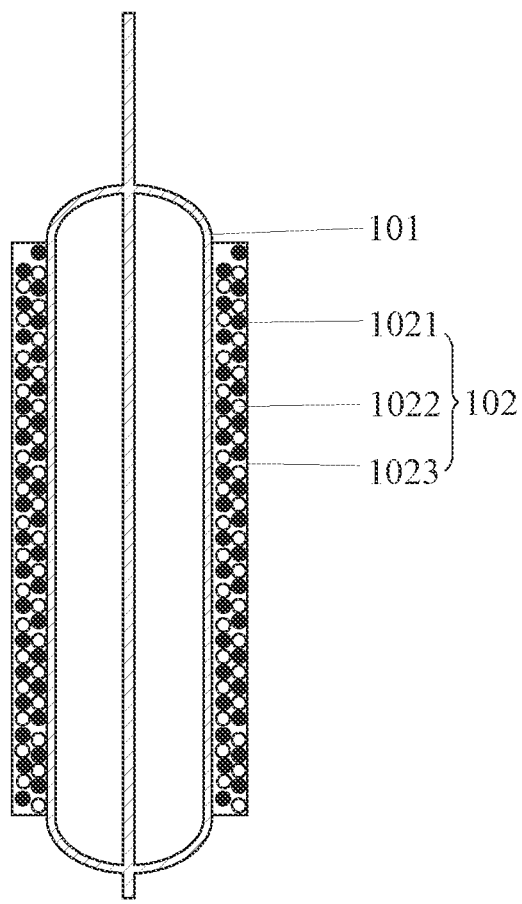
FIG. 1 is a schematic diagram of the structure of the drug coated balloon according to one embodiment of the present invention.

Referring to FIG. 1, the present invention provides a drug coated balloon, which includes a balloon body 101 and a drug loaded coating layer 102 coated on the outer surface of the balloon body 101. The drug loaded coating layer 102 is a non-hydrophilic structure, and the drug loaded coating layer 102 includes a first drug loaded coating component and a second drug loaded coating component 1023. The first drug loaded coating component includes at least two controllable sustained release drugs, and each controllable sustained release drug has different drug release kinetics. The second drug loaded coating component 1023 includes an active drug in a free unbound form and can be dispersed among different controllable sustained release drugs in the first drug loaded coating component, and also couples the controllable sustained release drugs onto the balloon body 101.

Exemplarily, the first drug loaded coating component consists of two controllable sustained release drugs, and the first drug loaded coating component includes a first controllable sustained release drug 1021 and a second controllable sustained release drug 1022, which have different drug release kinetics. For instance, the first controllable sustained release drug 1021 has a faster drug release rate, while the second controllable sustained release drug 1022 has a slower drug release kinetics, which is not limited however. The first and second controllable sustained release drugs 1021 and 1022 have diverse drug release kinetics, and their drug release rates can be adjusted through different combinations. This enables the drug coated balloon to provide bioactive drugs to the treatment site at various stages of the vascular restenosis cascade. It achieves the delivery of controllable, long-term therapeutic drugs to the diseased site, enhancing the overall vascular drug release efficacy.

It should be understood that the non-hydrophilic structures involved in the present invention include structures that are not water-soluble, as well as structures that do not contain hydrophilic molecules and structures that do not contain amphiphilic molecules. The first and second drug loaded coatings components of the present invention are non-hydrophilic structures, in other words, the controllable sustained release drugs are non-hydrophilic structures, and the active drug in a free unbound form is a non-hydrophilic structure. The non-hydrophilic structured drug loaded coating ensures the lipophilicity of the drug coating, thereby enhancing the drug transferring ability to the vascular wall, while also improving the drug resistance to blood flow washout or retention on the inner surface of the vessel.

In a preferred embodiment, the controllable sustained release drug is encapsulated in a polymer as a carrier to form drug loaded particles, and the polymer is biocompatible and biodegradable. Preferably, the polymer is a non-hydrophilic bioabsorbable polymer. Furthermore, the polymer is selected from at least one of the bioabsorbable polymers such as polylactic acid, polyglycolic acid, copolymers of lactic acid and glycolic acid, and polydioxanone. Preferably, polylactic acid or copolymers of lactic acid and glycolic acid are amorphous or semi-crystalline polymers. It is worth mentioning that the method of using polymers as carriers to encapsulate drugs to form drug loaded particles can be prepared by any applicable existing polymer encapsulated drug technology, such as microfluidic technology, and membrane emulsification technology, etc., which will not be specifically elaborated here.

It should be understood that the controllable sustained release drug discussed in the present invention refers to a drug with a controllable release rate, where the release rate of the drug can be controlled through the drug release kinetics. Different drug release kinetics has different drug release rates. The controllable sustained release drugs with different drug release kinetics may slowly release active drugs at different rates, thus such a drug loaded coating can provide the necessary therapeutic drugs for the mid and late stages of vascular restenosis cascade reactions, thereby avoiding explosive drug release and extinction. Therefore, by regulating the drug release kinetics, active drugs can be provided to the treatment site at different stages of the vascular restenosis cascade reaction, and rapid drug release and transfer to the diseased blood vessels can be achieved within a short duration of dilation time (usually 30-180 seconds). It is worth mentioning that different drug release kinetics can be achieved by certain manners. In the present invention, the different drug release kinetics of the controllable sustained release drugs may be regulated at least by using different types of polymers, using different molecular weights of polymers, controlling different ratios of polymer to drug, or controlling different ratios of surface area to volume of the drug loaded particles, which are not limited to these however. Preferably, the different release kinetics of the controllable sustained release drugs may be regulated by changing the ratio of polymer to drug. For example, the drug loading in a controllable sustained release drug is not less than 30% of the weight of the controllable sustained release drug, preferably 30-45%, and such a controllable sustained release drug has a fast drug release rate. The drug loading in the controllable sustained release drug is less than 30% of the weight of the sustained release drug, preferably 10-25%, and such a controllable sustained release drug has a relatively slow drug release rate.

In a preferred embodiment, the first drug loaded coating component includes a first controllable sustained release drug and a second controllable sustained release drug. The first controllable sustained release drug has a faster drug release rate, and the second controllable sustained release drug has slower drug release kinetics. By weight percentage, the drug loaded coating layer of the drug coated balloon includes 10%-30% of the first controllable sustained release drug, 20%-50% of the second controllable sustained release drug, and 20%-50% of the active drug in a free unbound form. In this embodiment, the release kinetics of the first controllable sustained release drug and the second controllable sustained release drug may be regulated by changing the ratio of polymer to drug. Specifically, the drug loading in the first controllable sustained release drug is not less than 30% by weight, preferably 30-45%, more preferably 35-45%, and the drug loading in the second controllable sustained release drug is less than 30% by weight, preferably 10-20%. Furthermore, the total drug dose of the drug loaded coating layer of the drug coated balloon may be 0.5 μg/mm$^2$ to 4 μg/mm$^2$ based on the effective surface area of the balloon, preferably 0.8 μg/mm$^2$ to 1.5 μg/mm$^2$.

It should be understood that the active drug in a free unbound form is considered as the only biologically active drug in terms of pharmacokinetics. In the present invention, the second drug loaded coating component, by using the active drug in the free unbound form, can provide a sufficient initial drug loading dosage to blood vessels that may be damaged during percutaneous vascular angioplasty while mechanical dilation. Furthermore, the active drugs in the free unbound forms are attached to the balloon body in the form of loosely separated drug particles, rather than dense drug membranes, and also dispersed among the controllable sustained released drugs in the first drug loaded coating component and coupled them onto the balloon body. It is worth mentioning that the free unbound active drugs may be but not limited to a type of pure drugs dissolved in a coating liquid mixture or particle forms added to the coating liquid mixture. Specifically, the coating liquid mixture may include but not be limited to a dispersion liquid, which should be a non-solvent of the polymer in the coating to ensure the stability of the drug loaded particles in the dispersion. Further, the coating liquid should also not have the ability to dissolute the active drug from the drug loaded particles to ensure the stability of the active drug in the drug loaded particles. In some embodiments, the dispersion liquid may be a single solvent or a mixture of multiple miscible solvents, and the solvent(s) may include but not limit to at least one of methanol, ethanol, isopropanol, n-hexane, heptane, petroleum ether, water, ethyl acetate, and acetone. Furthermore, the active drugs added into the coating liquid mixture in particle forms may be prepared by grinding, solvent/non-solvent precipitation method, and emulsion solvent evaporation method. Coating on the surface of the balloon body to form a drug coated layer can be done by methods such as spray coating, droplet deposition, and dip coating. Preferably, ultrasonic atomization spray coating technology is used to spray the suspension spray coating solution onto the balloon body to form a uniform drug coated layer. Furthermore, the content of the active drug in a free unbound form in the drug loaded coating layer of the balloon is 0%-60% of the total drug loading, preferably 20%-50%.

In a preferred embodiment, the drug or the active drug discussed in the present invention is sirolimus, also known as rapamycin, but it is not limited to this; of course, it can also be paclitaxel. As a unique drug component or one of the drug components, it can be selected based on the different physicochemical properties of the drug. In some embodiments, the first drug loaded coating component includes at least two controllable sustained release sirolimus with different drug release kinetics, and the second drug loaded coating component includes sirolimus in a free unbound form. On the one hand, sirolimus is safer and more effective in clinical practice, and on the other hand, the problem that sirolimus is difficult to transfer to the vascular wall due to its low lipophilicity is solved.

The following is a further explanation of the preparation method of the drug coated balloon in the present invention through specific embodiments, which is not limited, however.

Embodiment 1

A preparation method for a controllable sustained release drug with faster drug release kinetics was provided. The release kinetics of the controllable sustained release drugs was regulated and controlled by changing the ratio of polymer to drug. Sirolimus as the drug was taken as an example, and the specific preparation details include the following steps:
(1) a preparation of Solution 1: dissolving 300 mg of polymer (PLGA) and 200 mg of sirolimus in 10 ml of dichloromethane;
(2) a preparation of Solution 2: dissolving PVA in deionized water to make 2 wt. % PVA aqueous solution;
(3) a preparation of Solution 3: dissolving PVA in deionized water to make 1 wt. % PVA aqueous solution;
(4) adding 2 ml of Solution 1 into 6 ml of Solution 2 and homogenizing at a high speed of 10000 RPM for 1 minute to get Emulsion 1;
(5) adding Emulsion 1 into 45 ml of Solution 3 and homogenizing at a high speed of 10000 RPM for 3 minutes to form Emulsion 2;
(6) magnetically stirring Emulsion 2 at room temperature for at least 6 hours to remove solvent dichloromethane and refrigerated (at 4-10° C.) for 60 minutes;
(7) centrifuging and washing the microspheres with deionized ice water for multiple times; and
(8) suspending the microspheres in 5 ml of deionized water, freeze-dried and stored for use.

Embodiment 2

A preparation method for a controllable sustained release drug with slower drug release kinetics was provided. The release kinetics of the controllable sustained release drugs was regulated and controlled by changing the ratio of polymer to drug. Sirolimus as the drug was taken as an example, and the specific preparation details include the following steps:
(1) a preparation of Solution 1: dissolving 300 mg of polymer (PLGA) and 60 mg of sirolimus in 10 ml of dichloromethane;
(2) a preparation of Solution 2: dissolving PVA in deionized water to make 2 wt. % PVA aqueous solution;
(3) a preparation of Solution 3: dissolving PVA in deionized water to make 1 wt. % PVA aqueous solution;

(4) adding 2 ml of Solution 1 into 6 ml of Solution 2 and homogenizing at a high speed of 10000 RPM for 1 minute to get Emulsion 1;
(5) adding Emulsion 1 into 45 ml of Solution 3 and homogenizing at a high speed of 10000 RPM for 3 minutes to form Emulsion 2;
(6) magnetically stirring Emulsion 2 at room temperature for at least 6 hours to remove solvent dichloromethane and refrigerated (at 4-10° C.) for 60 minutes;
(7) centrifuging and washing the microspheres with deionized ice water for multiple times; and
(8) suspending the microspheres in 5 ml of deionized water, freeze-dried and stored for use.

Embodiment 3

A preparation method for an active drug in a free unbound form was provided. Sirolimus as the active drug was taken as an example, and the specific preparation details include the following steps:
(1) preparing 12 mg/ml sirolimus methanol solution;
(2) adding 60 ml of deionized water into a beaker of 100 ml, placing in an ultrasound water bath and ultrasound it at controlled low temperature;
(3) adding the sirolimus methanol solution dropwise into the deionized water with the mixing ratio of 1:12 by volume, introducing the sirolimus solution by using a syringe pump at a low flow rate of 0.2 ml/min;
(4) continuing to maintain the ultrasound for another 10 minutes; and
(5) centrifuging and washing the particulate drug with deionized ice water, and freeze-dried for use.

Embodiment 4

A preparation of a drug coated balloon includes:
(1) inflating the balloon body at moderate pressure;
(2) preparing a suspension spray coating solution by using the drug loaded microspheres prepared in Embodiment 1, Embodiment 2, and the drug particles prepared in Embodiment 3 into a coating solvent or a solvent combination at a solid weight percentage of 20%, 40%, and 40%, respectively; filling the suspension spray coating solution into the syringe and homogenized with magnetic stirring the either inside the syringe chamber or from outside of the syringe barrel; and spray coating onto a rotating inflated balloon body by ultrasonic atomization;
(3) after coating, drying and folding the balloon, and placing into a protecting sheath; sterilizing the drug coated balloon with ethylene oxide.

Embodiment 5

A vitro simulation testing was performed on the drug coated balloon prepared in Embodiment 4, as follows.
Freshly harvested coronary vessels were provided and rinsed with sterile saline for multiple times. The blood vessels were cut to an appropriate length and connected to the distal end of the simulated vascular curvature channel as in ASTM F2394-07. The proximal end of the simulated vascular channel was connected to circulation of physiological saline of 37° C. via a three-way valve, and the flow rate was controlled by a peristaltic pump at 50 ml/min. The simulated vascular channel was flushed with saline of 37° C. in advance.

The protective sheath of the drug coated balloon was removed, and the balloon was inserted from the proximal end of the simulated vascular channel, tracked through the simulated vascular channel and reached the blood vessel within 60±10 seconds. The drug coated balloons were inflated in the lumen of the blood vessel at 8 atm for 60 seconds to transfer the drug containing coating to the vessel lumen. After retraction and withdrawal from the vascular curvature channel, the simulated vascular channel together with the blood vessel was flushed with 37° C. saline for 1 hour, with a flow rate of 50 ml/min.

Figure 2:
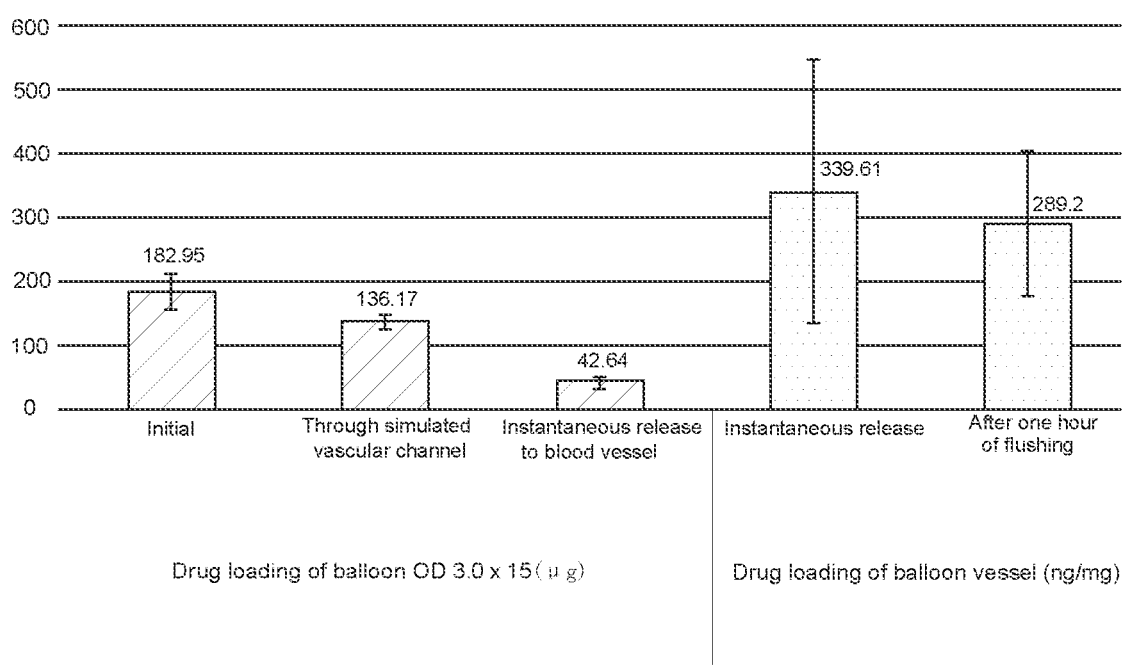
FIG. 2 shows the result of in vitro simulation testing of the product according to an embodiment of the present invention.

The test results are shown in FIG. 2. The drug loading of the drug coated balloon was 1.3 μg/mm² in this test. The drug concentration in blood vessel reached 289.2 ng/mg after 1 hour of simulated postoperative flushing. The drug loss of the balloon through tracking the simulated vascular channel was 25.6%, indicating that the drug loaded coated layer of the drug coated balloon of the present invention has superior drug release efficacy.

Embodiment 6

Simulate use particulate formation testing was performed on the drug coated balloon prepared in Embodiment 4, as follows.
Freshly harvested coronary vessels were provided and rinsed with sterile saline multiple times. The blood vessels were cut to an appropriate length and connected to the distal end of the simulated vascular curvature channel as in ASTM F2394-07. The proximal end of the simulated vascular channel was connected to circulation of physiological saline of 37° C. via a three-way valve, and the flow rate was controlled by a peristaltic pump at 50 ml/min. The simulated vascular channel was flushed with saline of 37° C. in advance.

The protective sheath of the drug coated balloon was removed, and the balloon was inserted from the proximal end of the simulated vascular channel, tracked through the simulated vascular channel and reached the blood vessel within 60±10 seconds. The drug coated balloons were inflated in the lumen of the blood vessel at 8 atm for 60 seconds to transfer the drug containing coating to the vessel lumen. After retraction and withdrawal from the vascular curvature channel, the simulated vascular channel together with the blood vessel were flushed with saline for 1 hour at 37° C., with a flow rate of 50 ml/min.

100 ml of the liquid was collected at the distal end of the blood vessel starting from the beginning of saline flushing. The liquid was used for particle measurements with a light obscuration particle counting test. As shown in Table 1, the drug coated balloon prepared by the present technology produced low number of particles during simulated use, especially no particles greater than or equal to 100 μm were generated.

TABLE 1

Test results of insoluble particles

| Particle | DCB: OD3.0 × 15 (mm) | |
|---|---|---|
| | Average | Maximum |
| ≥10 μm | 23850 | 25220 |
| ≥25 μm | 800 | 1000 |
| ≥50 μm | 20 | 40 |
| ≥100 μm | 0 | 0 |

The above disclosures are only the preferred embodiments of the present invention, and of course, it cannot be used to limit the scope of rights in the present invention. Therefore, equivalent changes made according to the scope of the patent in the present invention still fall within the scope of the present invention.

What is claimed is:

1. A drug coated balloon, comprising a balloon body and a drug loaded coating layer coated on an outer surface of the balloon body,
   wherein the drug loaded coating layer comprises:
   a first drug loaded coating component comprising at least two controllable sustained release drugs with different drug release kinetics; and
   a second drug loaded coating component comprising an active drug in a free unbound form, dispersed among different controllable sustained release drugs in the first drug loaded coating component and coupling the controllable sustained release drugs onto the balloon body,
   wherein both the first drug loaded coating component and the second drug loaded coating component are non-hydrophilic compositions,
   wherein the active drug in a free unbound form directly couples the controllable sustained release drugs onto the balloon body, without any additional binding matrix, and
   wherein the active drug in a free unbound form is attached to the balloon body in a form of separated drug particles, rather than in a form of drug membranes.

2. The drug coated balloon according to claim 1, wherein the active drug in a free unbound form is processed by dissolving a pure drug of the active drug in a dispersion liquid or adding a particle form of the active drug to the dispersion liquid.

3. The drug coated balloon according to claim 2, wherein the dispersion liquid comprises at least one of methanol, ethanol, isopropanol, n-hexane, heptane, petroleum ether, water, ethyl acetate, and acetone.

4. The drug coated balloon according to claim 1, wherein each of the controllable sustained release drugs is encapsulated in a polymer as a carrier to form drug loaded particles, and the polymer is biocompatible and bioabsorbable.

5. The drug coated balloon according to claim 4, wherein the polymer is selected from at least one of polylactic acid, polyglycolic acid, a copolymer of lactic acid and glycolic acid, and polydioxanone.

6. The drug coated balloon according to claim 4, wherein the different drug release kinetics of the controllable sustained release drugs is regulated at least by: using different types of polymers, using different molecular weights of polymers, controlling different ratio of polymer to drug, or controlling different ratio of surface area to volume of the drug loaded particles.

7. The drug coated balloon according to claim 4, wherein the first drug loaded coating component comprises a first controllable sustained release drug and a second controllable sustained release drug, a drug loading of the first controllable sustained release drug is not less than 30% by weight, and a drug loading of the second controllable sustained release drug is less than 30% by weight.

8. The drug coated balloon according to claim 7, wherein the drug loading of the first controllable sustained release drug is 30-45% by weight, and the drug loading of the second controllable sustained release drug is 10-20% by weight.

9. The drug coated balloon according to claim 7, wherein by weight percentage, the drug loaded coating layer is constituted by 10%-30% from the first controllable sustained release drug, 20%-50% from the second controllable sustained release drug, and 20%-50% from the active drug in a free unbound form.

10. The drug coated balloon according to claim 1, wherein the first drug loaded coating component comprises at least two controllable sustained release sirolimus, and the second drug loaded coating component comprises sirolimus in a free unbound form.

* * * * *